United States Patent
Norcini et al.

(10) Patent No.: US 6,548,480 B1
(45) Date of Patent: Apr. 15, 2003

(54) PHOSPHONIC ACID DERIVATIVES WITH METALLOPEPTIDASE INHIBITORY ACTIVITY

(75) Inventors: Gabriele Norcini, Vizzola Ticino; Daniela Botta, Como; Francesco Santangelo, Milan, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/068,107

(22) PCT Filed: Nov. 11, 1996

(86) PCT No.: PCT/EP96/04911

§ 371 (c)(1),
(2), (4) Date: May 4, 1998

(87) PCT Pub. No.: WO97/19102

PCT Pub. Date: May 29, 1997

(30) Foreign Application Priority Data

Nov. 23, 1995 (IT) .......................................... MI95A2430

(51) Int. Cl.$^7$ ............................................... A61K 38/05
(52) U.S. Cl. .......................... 514/19; 562/445; 562/575
(58) Field of Search ........................... 514/19; 562/445, 562/575

(56) References Cited

U.S. PATENT DOCUMENTS 4,432,972 A * 2/1984 Karanewsky

OTHER PUBLICATIONS

Wilson (Cardiovascular Research 42 (3) 761–72, 1999).*
Koerner (Journal of Cardiovascular Pharmacology 17 (2) 185–91, 1991).*
Linz (Journal of Cardiovascular Pharmacology 15 Suppl 6 S99–109, 1990).*
Billuaud_Mesguich E (Revue fe Medecine Interne 7 (5) 543_7, 1986).*
Huckle W R (Circulation 93 (5) 1009–19, 1996).*
Edling, Oliver (Journal of Pharmacology and Experimental Therapeutics 275 (2), 854–863, 1995).*
Grover G.J. (J Pharmacol Exp Ther 257 (3), 919–929, 1991).*
Gennaro (Remington: The Science and Practice of Pharmacy, pp. 665–671 Mack Publishing, 19th Edition, 1995.*

* cited by examiner

Primary Examiner—Christopher S. F. Low
Assistant Examiner—David Lukton
(74) Attorney, Agent, or Firm—Arent Fox Kintner Plotkin & Kahn PLLC

(57) ABSTRACT

Compounds of formula (I) wherein R is an alkyl, aryl or arylalkyl group wherein the aryl is phenyl naphthyl or heterocycle; $R_1$ and $R_2$, the same or different, are hydrogen atoms or alkyl groups; $R_3$ is an aryl or arylalkyl group wherein the aryl is as above; $R_4$ is a heterocycle optionally substituted with a heterocycle or phenyl, or it is a phenyl group substituted with a heterocycle ($R_4$ is not imidazole or indole); X is a bond or —OCONH or —CONH— group, processes for their preparation and pharmaceutical compositions thereof, are described. The compounds of formula (I) are endowed with a dual ACE-inhibitory and NEP-inhibitory activity and are useful in the treatment of cardiovascular disease.

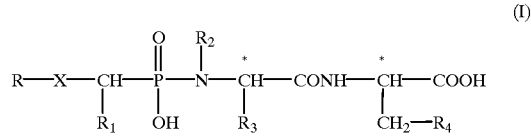

(I)

8 Claims, No Drawings

PHOSPHONIC ACID DERIVATIVES WITH METALLOPEPTIDASE INHIBITORY ACTIVITY

The present invention relates to phosphonic acid derivatives useful in the treatment of cardiovascular diseases and, more particularly, it relates to phosphonic acid derivatives useful in the treatment of cardiovascular diseases as metallopeptidase inhibitors. The pharmacologic interest towards the study of metallopeptidase inhibitory molecules derives from the role that said enzymes exert on the level of the cardiocirculatory system.

It is well-known in fact that compounds with angiotensin converting enzyme (ACE) inhibitory activity are mainly useful in the treatment of hypertension, of heart failure and of post-infarct in that they inhibit the formation of angiotensin II, a substance which increases the blood pressure.

Compounds with endothelin converting enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase (NEP) enzyme, also called enkephalinase, are useful as vasodilators and diuretics in that the NEP enzyme is responsible for the inactivation, not only of endogenous enkephahne, but also of some natriuretic factors among which, for instance, the atrial natriuretic factor (ANF), a vasodilating hormone secreted by heart.

Therefore, even exerting their action on the cardiovascular system with different mechanisms of action, the compounds with metallopeptidase inhibitory activity are generally used, alone or in combination, in the treatment of hypertension, renal failure, congestive heart failure and post-infarct.

In the U.S. Pat. No. 4,432,972 (E.R. Squibb & Sons, Inc.) phosphorylated derivatives of amino acids such as, in particular, phosphonamidates endowed with ACE-inhibitory and enkephahnase-inhibitory activity were described.

Said compounds were described as useful hypotensive and analgesic agents. In the European patent application No. 0518299 (Takeda Chemical Industries, Ltd) some phosphonic acid derivatives, endowed with ECE-inhibitory activity, usefull in the treatment of hypertension, of cardiac or cerebrovascular diseases and of renal diseases were described.

Now we have found phosphonic acid derivatives which are endowed with inhibitory activity on the angiotensin converting enzyme as well as on the neutral endopeptidase enzyme (dual ACE/NEP-inhibitory activity) which renders them particularly useful in the cardiovascular therapy.

Therefore object of the present invention are the compounds of formula

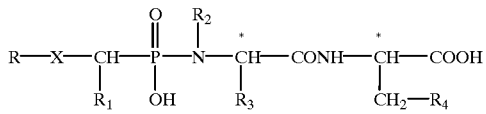

(I)

wherein
R is a straight or branched $C_1$–$C_6$ alkyl group optionally substituted with one or more fluorine atoms, an aryl or arylalkyl group with from 1 to 6 carbon atoms in the alkyl moiety wherein the aryl is a phenyl 1-naphthyl, 2-naphthyl group or a 5 or 6 membered aromatic heterocycle with 1 or 2 heteroatoms selected among nitrogen, oxygen and sulphur, optionally substituted with one or more substituents, the same or different, selected among halogen atoms, hydroxy groups, alkyl, alkoxy, alkythio, alkylsulphonyl or alkoxycarbonyl groups with from 1 to 3 carbon atoms in the alkyl moiety, carboxy groups, aminocarbonyl groups, acylamino groups, aminosulphonyl groups, mono- or di-alkylaminocarbonyl groups with from 1 to 3 carbon atoms in the alkyl moiety;

$R_1$ and $R_2$, the same or different, represent a hydrogen atom or a straight or branched $C_1$–$C_4$ alkyl group;

$R_3$ is a straight or branched $C_1$–$C_6$ alkyl group or an arylalkyl group with from 1 to 6 carbon atoms in the alkyl moiety wherein the aryl is a phenyl, 1-naphthyl 2-naphthyl group or a 5 or 6 membered aromatic heterocycle with one or two heteroatoms selected among nitrogen, oxygen and sulphur, optionally substituted as indicated for R;

$R_4$ is a 5 or 6 membered aromatic heterocyclic group with one or two heteroatoms selected among nitrogen, oxygen and sulphur, optionally substituted with a 5 or 6 membered aromatic heterocyclic group with one or two heteroatoms selected among nitrogen, oxygen and sulphur or with a phenyl group, or it is a phenyl group substituted with a 5 or 6 membered aromatic heterocyclic group with one or two heteroatoms selected among nitrogen, oxygen and sulphur, being the phenyl and the heterocyclic groups optionally substituted with one or more substituents, the same or different, selected among halogen atoms, alkyl alkoxy, alkylthio or alkoxycarbonyl groups with from 1 to 3 carbon atoms in the alkyl moiety;

X is a single bond or an —O—CONH— or —CONH— group;

the carbon atoms marked with an asterisk are asymmetric carbon atoms;

and pharmaceutically acceptable salts thereof;
provided that $R_4$ is not an imidazolyl or indolyl group.

The compounds of formula I contain at least two asymmetric carbon atoms and can thus exist in the form of stereoisomers.

Therefore, object of the present invention are the compounds of formula I in the form of stereoisomeric mixture as well as in the form of single stereoisomers.

The compounds of formula I object of the present invention are endowed with a dual ACE/NEP-inhibitory activity and are useful in the treatment of cardiovascular diseases.

In the present description, unless otherwise specified, with the term alkyl group we intend a straight or branched alkyl such as methyl, ethyl, n.propyl, isopropyl, n.butyl, sec-butyl tert-butyl isobutyl n.pentyl 2-pentyl, 3-pentyl, isopentyl, tert-pentyl n.hexyl and isohexyl; with the term alkoxy group we intend a straight or branched alkoxy such as methoxy, ethoxy, n.propoxy and isopropoxy; with the term halogen atom we intend a fluorine, chlorine, bromine or iodine atom; with the term acyl we intend an acyl group deriving from an aliphatic or aromatic carboxylic acid such as acetic, propionic, butyric and benzoic acid; with the term aryl we intend an aromatic group such as phenyl, 1-naphthyl, 2-naphthyl or a 5 or 6 membered heterocyclic group containing 1 or 2 heteroatoms selected among nitrogen, oxygen and sulphur such as thiazole, isoxazole, oxazole, isothiazole, pyrazole, imidazole, thiophene, pyrrole, pyridine, pyrimidine, pyrazine and furan, optionally benzocondensed.

Examples of pharmaceutically acceptable salts of the compounds of formula I are the salts with alkali or alkali-earth metals and the salts with pharmaceutically acceptable organic bases.

Preferred compounds of formula I are the compounds wherein $R_4$ represents a phenyl group substituted in position 4 with a heterocyclic group.

Particularly preferred, in this class, are the compounds of formula I wherein $R_1$ and $R_2$ represent a hydrogen atom and $R_3$ represents a straight or branched $C_1$–$C_4$ alkyl group.

Preferred examples of pharmaceutically acceptable salts of the compounds of formula I are the salts with alkali metals such as sodium, lithium and potassium.

Specific examples of preferred compounds of formula I, object of the present invention, are:

N-(N'-propylphosphonyl-leucyl)-[4-(2-furyl)]-phenylalanine;
N-(N'-propylphosphonyl-leucyl)-[4-(3-furyl)]-phenylalanine;
N-(N'-propylphosphonyl-leucyl)-[4-(2-thienyl)]-phenylalanine;
N-(N'-propylphosphonyl-leucyl)-[4-(3-thienyl)]-phenylalanine;
N-(N'-propylphosphonyl-leucyl)-[4-(N"-methyl-2-pyrrolyl)]-phenylalanine;
N-(N'-propylphosphonyl-leucyl)-[4-(N"-methyl-3-pyrrolyl)]-phenylalanne;
N-(N'-propylphosphonyl-leucyl)-[4-(2-thiazolyl)]-phenylalanine;
N-(N'-propylphosphonyl-leucyl)-[4-(2-pyridyl)]-phenylalanine;
N-(N'-propylphosphonyl-leucyl)-[4-(3-pyridyl)]-phenylalanine;
N-(N'-propylphosphonyl-leucyl)-(4-pyrazinyl)-phenylalanine;
N-(N'-propylphosphonyl-leucyl)-[4-(5-pyrmidinyl)]-phenylalanine;
N-(N'-propylphosphonyl-valyl)-[4-(2-furyl)]-phenylalaine;
N-(N'-propyhphosphonyl-valyl)-[4-(3-furyl)]-phenylalanine;
N-(N'-propyhphosphonyl-valyl)-[4-(2-thienyl)]-phenylalanine;
N-(N'-propylphosphonyl-valyl)-[4-(3-thienyl)]-phenylalanine;
N-(N'-propylphosphonyl-valyl)-[4-(N"-methyl-2-pyrrolyl)]-phenylalanine;
N-(N'-propylphosphonyl-valyl)-[4-(N"-methyl-3-pyrrolyl)]-phenylalanine;
N-(N'-propylphosphonyl-valyl)-[4-(2-thiazolyl)]-phenylalanine;
N-(N'-propylphosphonyl-valyl)-[4-(2-pyridyl)]-phenylalanine;
N-(N'-propylphosphonyl-valyl)-[4-(3-pyridyl)]-phenylalanine;
N-(N'-propylphosphonyl-valyl)(4-pyrazinyl)-phenylalanine;
N-(N'-propylphosphonyl-valyl)-[4-(5-pyrimidinyl)]-phenylalanine;
N-[N'-(2-thienylmethyl)phosphonyl-leucyl]-[4-(2-furyl)]-phenylalanine;
N-[N'-(2-thienylmethyl)phosphonyl-leucyl]-[4-(3-fiuyl)]-phenylalanine;
N-[N'-(2-thienylmethyl)phosphonyl-leucyl]-[4-(2-thienyl)]-phenylalanine;
N-[N'-(2-thienylmethyl)phosphonyl-leucyl]-[4-(3-thienyl)]-phenylalanine;
N-[N'-(2-thienylmethyl)phosphonyl-leucyl]-[4-(N"-methyl-2-pyrrolyl)]-phenylalanine;
N-[N'-(2-thienylmethyl)phosphonyl-leucyl]-[4-(N"-methyl-3-pyrrolyl)]-phenylalanine;
N-[N'-(2-thienylmethyl)phosphonyl-leucyl]-[4-(2-thiazolyl)]-phenylalanine;
N-[N'-(2-thienylmethyl)phosphonyl-leucyl]-[4-(2-pyridyl)]-phenylalanine;
N-[N'-(2-thienylmethyl)phosphonyl-leucyl]-[4-(3-pyridyl)]-phenylalanine;
N-[N'-(2-thienylmethyl)phosphonyl-leucyl]-(4-pyrazinyl)-phenylalanine;
N-[N'-(2-thienylmethyl)phosphonyl-leucyl]-[4-(5-pyrimidinyl)]-phenylalanine;
N-[N'-(2-thienylmethyl)phosphonyl-valyl]-[4-(2-furyl)]-phenylalanine;
N-[N'-(2-thienylmethyl)phosphonyl-valyl]-[4-(3-furyl)]-phenylalanine;
N-[N'-(2-thienyhnethyl)phosphonyl-valyl]-[4-(2-thienyl)]-phenylalanine;
N-[N'-(2-thienylmethyl)phosphonyl-valyl]-[4-(3-thienyl)]-phenylalanine;
N-[N'-(2-thienylmethyl)phosphonyl-valyl]-[4-(N"-methyl-2-pyrrolyl)]-phenylalanine;
N-[N'-(2-thienylmethyl)phosphonyl-valyl]-[4-(N"-methyl-3-pyrrolyl)]-phenylalanine;
N-[N'-(2-thienylmethyl)phosphonyl-valyl]-[4-(2-thiazolyl)]-phenylalanine;
N-[N'-(2-thienylmethyl)phosphonyl-valyl]-[4-(2-pyridyl)]-phenylalanine;
N-[N'-(2-thienylmethyl)phosphonyl-valyl]-[4-(3-pyridyl)]-phenylalanine;
N-[N'-(2-thienyhmethyl)phosphonyl-valyl]-(4-pyrazinyl)-phenylalanine;
N-[N'-(2-thienylmethyl)phosphonyl-valyl]-[4-(5-pyrmidinyl)]-phenylalanine;
N-[N'-(benzyloxycarbonylaminomethyl)phosphonyl-leucyl]-[4-(2-furyl)]-phenylalanine;
N-[N'-(benzyloxycarbonylaminomethyl)phosphonyl-leucyl]-[4-(3-furyl)]-phenylalanine;
N-[N'-(benzyloxycarbonylaminomethyl)phosphonyl-leucyl]-[4-(2-thienyl)]-phenylalanine;
N-[N'-(benzyloxycarbonylaminomethyl)phosphonyl-leucyl]-[4-(3-thienyl)]-phenylalanine;
N-[N'-(benzyloxycarbonylaminomethyl)phosphonyl-leucyl)-[4-(N"methyl-2-pyrrolyl)]-phenylalanine;
N-[N'-(benzyloxycarbonylaminomethyl)phosphonyl-leucyl]-[4-(N"-methyl-3-pyrrolyl)]-phenylalanine;
N-[N'-(benzyloxycarbonylaminomethyl)phosphonyl-leucyl]-[4-(2-thiazolyl)]-phenylalanine;
N-[N'-(benzyloxycarbonylaminomethyl)phosphonyl-leucyl]-[4-(2-pyridyl)]-phenylalanine;
N-[N'-(benzyloxycarbonylaminomethyl)phosphonyl-leucyl]-[4-(3-pyridyl)]-phenylalanine;
N-[N'-(benzyloxycarbonylaminomethyl)phosphonyl-leucyl]-(4-pyrazinyl)-phenylalanine;
N-[N'-(benzyloxycarbonylaminomethyl)phosphonyl-leucyl]-[4-(5-pyrimidinyl)]-phenylalanine;
N-[N'-(benzyloxycarbonylaminomethyl)phosphonyl-valyl]-[4-(2-furyl)]-phenylalanine;
N-[N'-(benzyloxycarbonylaminomethyl)phosphonyl-valyl]-[4-(3-furyl)]-phenylalanine;
N-[N'-(benzyloxycarbonylaminomethyl)phosphonyl-valyl]-[4-(2-thienyl)]-phenylalanine;
N-[N'-(benzyloxycarbonylaminomethyl)phosphonyl-valyl]-[4-(3-thienyl)]-phenylalanine;
N-[N'-(benzyloxycarbonylaminomethyl)phosphonyl-valyl]-[4-(N"-methyl-2-pyrrolyl)]-phenylalanine;
N-[N'-(benzyloxycarbonylaminomethyl)phosphonyl-valyl]-[4-(N"-methyl-3-pyrrolyl)]-phenylalanine;
N-[N'-(benzyloxycarbonylaminomethyl)phosphonyl-valyl]-[4-(2-thiazolyl)]-phenylalanine;
N-[N'-(benzyloxycarbonylaminomethyl)phosphonyl-valyl]-[4-(2-pyridyl)]-phenylalanine;

N-[N'-(benzyloxycarbonylaminomethyl)phosphonyl-valyl]-[4-(3-pyridyl)]-phenylalanine;
N-[N'-(benzyloxycarbonylaminomethyl)phosphonyl-valyl]-(4-pyrazinyl)-phenylalanine;
N-[N'-(benzyloxycarbonylaminomethyl)phosphonyl-valyl]-[4-(5-pyrimidinyl)]-phenylalanine;
N-[N'-(acetylaminomethyl)phosphonyl-leucyl]-[4-(2-furyl)]-phenylalanine;
N-[N'-(acetylaminomethyl)phosphonyl-leucyl]-[4-(3-furyl)]-phenylalanine;
N-[N'-(acetylaminomethyl)phosphonyl-leucyl]-[4-(2-thienyl)]-phenylalanine;
N-[N'-(acetylaminomethyl)phosphonyl-leucyl]-[4-(3-thienyl)]-phenylalanine;
N-[N'-(acetylaminomethyl)phosphonyl-leucyl]-[4-(N''-methyl-2-pyrrolyl)]-phenylalanine;
N-[N'-(acetylaminomethyl)phosphonyl-leucyl]-[4-(N''-methyl-3-pyrrolyl)]-phenylalanine;
N-[N'-(acetylaminomethyl)phosphonyl-leucyl]-[4-(2-thiazolyl)]-phenylalanine;
N-[N'-(acetylaminomethyl)phosphonyl-leucyl]-[4-(2-pyridyl)]-phenylalanine;
N-[N'-(acetylaminomethyl)phosphonyl-leucyl]-[4-(3-pyridyl)]-phenylalanine;
N-[N'-(acetylaminomethyl)phosphonyl-leucyl]-(4-pyrazinyl)-phenylalanine;
N-[N'-(acetylaminomethyl)phosphonyl-leucyl]-[4-(5-pyrimidinyl)]-phenylalanine;
N-[N'-(acetylaminomethyl)phosphonyl-valyl]-[4-(2-furyl)]-phenylalanine;
N-[N'-(acetylaminomethyl)phosphonyl-valyl]-[4-(3-furyl)]-phenylalanine;
N-[N'-(acetylaminomethyl)phosphonyl-valyl]-[4-(2-thienyl)]-phenylalanine;
N-[N'-(acetylaminomethyl)phosphonyl-valyl]-[4-(3-thienyl)]-phenylalanine;
N-[N'-(acetylaminomethyl)phosphonyl-valyl]-[4-(N''-methyl-2-pyrrolyl)]-phenylalanine;
N-[N'-(acetylaminomethyl)phosphonyl-valyl]-[4-(N''-methyl-3-pyrrolyl)]-phenylalanine;
N-[N'-(acetylaminomethyl)phosphonyl-valyl]-[4-(2-thiazolyl)]-phenylalanine;
N-[N'-(acetylaminomethyl)phosphonyl-valyl]-[4-(2-pyridyl)]-phenylalanine;
N-[N'-(acetylaminomethyl)phosphonyl-valyl]-[4-(3-pyridyl)]-phenylalanine;
N-[N'-(acetylaminomethyl)phosphonyl-valyl]-(4-pyrazinyl)-phenylalanine;
N-[N'-(acetylaminomethyl)phosphonyl-valyl]-[4-(5-pyrimidinyl)]-phenylalanine.

The preparation of the compounds of formula I, object of the present invention, comprises the reaction between a phosphorylated derivative of formula

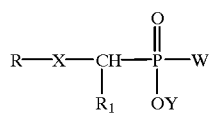
(II)

wherein

R, $R_1$ and X have the above reported meanings, W represents a halogen atom, preferably chlorine, and Y represents a protective group, preferably a $C_1$–$C_4$ alkyl, a phenyl or a phenylalkyl with from 1 to 4 carbon atoms in the alkyl moiety;

and a dipeptide derivative of formula

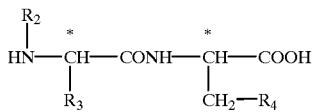
(III)

wherein $R_2$, $R_3$ and $R_4$ have the above reported meanings.

The phosphorylated derivative of formula II can be prepared from the corresponding compound of formula

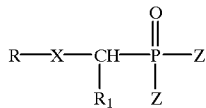
(IV)

wherein

R, $R_1$ and X have the above reported meanings and the Z groups both represent a W or OY group wherein W and Y have the above reported meanings.

The preparation of the compounds of formula II from the corresponding compounds of formula IV is carried out according to conventional techniques, by reaction with a halogenating agent or with a compound of formula YOH, wherein Y has the above reported meanings.

For a reference to the preparation of the compounds of formula II wherein X is a single bond or an —O—CONH— group see, for instance, D. S. Karanewsky et at, J. Med. Chem. 1988, 31, 204–212 and B. P. Morgan et al, J. Am Chem. Soc. 1991, 113, 297–307.

The compounds of formula II wherein X is a —CONH— group can be prepared, as example, from the corresponding compounds of formula II wherein X is an —O—CONH— group and R=benzyl through hydrogenolysis of the carbamic group (R—O—CONH—) and subsequent reaction with a compound of formula

(V)

wherein

R has the above reported meanings and $W_1$ represents a chlorine or bromine atom.

The dipeptide derivatives of formula III, in their turn, can be prepared through the condensation between an amino acid of formula

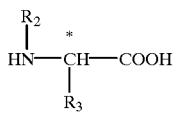
(VI)

wherein

R$_2$ and R$_3$ have the above reported meanings; and an alanine derivative of formula

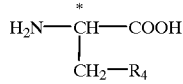

(VII)

wherein R$_4$ has the above reported meanings.

The condensation reaction is carried out according to conventional techniques of the chemistry of peptides.

Before carrying out the reaction it can be useful to properly protect the optional functional groups which could interfere in the reaction.

The optional protection is carried out according to conventional techniques.

For instance, in the reaction between the phosphorylated derivative of formula II and the dipeptide derivative of formula III it can be useful to protect the free carboxy function of the compound of formula III as well as the hydroxy function of the phosphonic group.

Likewise, in the reaction between the amino acid of formula VI and the alanine derivative of formula VII, it can be useful to protect the amino function of the derivative of formula VI and the carboxy function of the derivative of formula VII.

The evaluation of the usefulness of the optional protection as well as the selection of the kind of adopted protection according to the reaction to be carried out and to the functional groups to be protected are within the normal knowledge of the man skilled in the art.

The removal of the optional protective groups is carried out according to conventional techniques.

For a general reference to the use of protective groups in organic chemistry see Theodora W. Greene and Peter G. M. Wuts "Protective Groups in Organic Synthesis", John Wiley & Sons, Inc., II Ed., 1991.

The compounds of formula VI and VII are known or easily prepared according to known methods.

For a reference to the preparation of the compounds of formula VII see, for instance, the synthetic methods described by W. C. Shieh and T. R. Bailey in J. Org. Chem. 1992, 57, 379–381 and Tetrahedron Letters, 27, 4407–4410, 1986, respectively.

The compounds of formula I, object of the present invention, can be further prepared according to an alternative synthetic scheme comprising the reaction between a phosphorylated derivative of formula

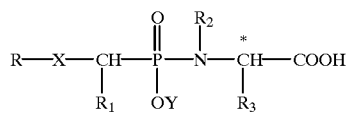

(VIII)

wherein

R, R$_1$, R$_2$, R$_3$, X and Y have the above reported meanings; and an alanine derivative of formula VII.

Analogously to what previously reported, also in the above reaction it can be useful to protect, according to conventional techniques, eventual functional groups which could interfere in the reaction.

The compounds of formula VIII are known or easily prepared according to known methods.

For instance, the compounds of formula VIII can be prepared through the reaction between the phosphorylated derivative of formula II and the amino acid of formula VI according to conventional methods of the chemistry of peptides.

In view of what above indicated, it is clear to the man skilled in the art that the preparation of the compounds of formula I wherein X is a —CONH— group can be optionally carried out starting from the corresponding compounds of formula I wherein X is an —O—CONH— group and R=benzyl, prepared according to one of the aforementioned synthetic methods.

The compounds of formula I in the form of single stereoisomers are prepared by stereo selective synthesis or by separation of the stereoisomeric mixture according to conventional techniques.

Also the preparation of the salts of the compounds of formula I, object of the invention, is carried out according to conventional techniques.

The compounds of formula I object of the present invention are endowed with a dual ACE/NEP-inhibitory activity and are useful in the treatment of cardiovascular diseases.

The inhibitory activity of the compounds of formula I, in particular, was evaluated by means of in vitro and ex vivo tests.

The in vitro inhibitory activity of the compounds of formula I was evaluated in comparison to known molecules endowed with ACE-inhibitory or NEP-inhibitory activity (example 3).

Captopril, a drug known as the first orally active ACE-inhibitor (The Merck Index, XI ed.—No. 1773, pages 267–268), was used as a comparison compound for the ACE-inhibitory activity.

Thiorphan [DL-(3-mercapto-2-benzylpropionyl)glycine] instead, known molecule considered the parent compound for NEP-inhibitors and described for the first time by Roques et al. in Nature, vol. 288, pages 286–288, (1980), was used as a comparison compound for the NEP-inhibitory activity.

N-[N'-(4-phenyl)butylphosphonyl-L-phenylalanyl]-L-phenylalanine dilithium salt (hereinafter referred to as compound R-1), exemplified in the aforementioned U.S. Pat. No. 4,432,972, was considered as a further comparison compound for evaluating the in vitro inhibitory activity of the compounds of formula I.

The in vitro inhibitory activity of the compounds of formula I, expressed as IC$_{50}$ value, is pharmacologically significant in that it results at nM concentrations.

Said activity resulted to be at least comparable to that of Captopril, to what it concerns the ACE-inhibitory activity, and to that of Thiorphan, to what it concerns the NEP-inhibitory activity.

With respect to the compound R-1, moreover, the dual ACE/NEP-inhibitory activity of the compounds of formula I resulted to be significantly higher.

As above indicated, the inhibitory activity of the compounds of formula I was evaluated also by means of ex vivo experiments, using the aforementioned compound R-1 as a comparison compound (example 4).

The dual ACE/NEP-inhibitory activity ex vivo of the compounds of formula I resulted to be significantly higher than that of the comparison compound.

For a practical use in therapy, the compounds of formula I can be formulated in solid or liquid pharmaceutical compositions, suitable to oral or parenteral administration.

Therefore, the pharmaceutical compositions containing a therapeutically effective amount of a compound of formula I in admixture with a carrier for pharmaceutical use are a further object of the present invention.

Specific examples of pharmaceutical compositions according to the present invention are tablets, coated tablets, capsules, granulates, solutions and suspensions suitable to oral administration, solutions and suspensions suitable to parenteral administration.

The pharmaceutical compositions object of the present invention are prepared according to conventional techniques.

Although the compounds of formula I are active as such, with the aim to satisfy particular therapeutic or pharmaceutical properties, it can be useful to transform them into the corresponding biologic precursors (pro-drugs).

Therefore, according to the conventional techniques for the preparation of pro-drugs of phosphorylated and amido derivatives, suitable pro-drugs can be obtained for instance through the esterification of the carboxy function or of the phosphonic function.

Also the compounds of formula I in the form of pro-drugs and, in particular, the compounds obtained through the esterification of the carboxy or phosphonic function, as well as the pharmaceutical compositions which contain the compounds of formula I in the form of pro-drugs and, in particular, which contain the compounds of formula I wherein the carboxy or phosphonic group results to be esterified, are within the scope of the present invention.

The daily dose of the compound of formula I or of the corresponding pro-drug will depend on several factors such as the seriousness of the disease, the individual response of the patient or the kind of formulation but it is usually comprised between 0.01 mg and 20 mg per kg of body weight divided into a single dose or into more daily doses.

With the aim of illustrating the present invention the following examples are now given.

Unless otherwise specified, the flash chromatographies were carried out by using flash chromatography silica gel from Baker company (code 7024-00).

REFERENCE EXAMPLE 1

N-[N'-(4-phenyl)butylphosphonyl-L-phenlalanyl]-L-phenylalanine dilithium salt (Compound R-1)

Said compound was prepared according to the procedure described in U.S. Pat. No. 4,432,972 (example 36).

EXAMPLE 1

N-(N'-propylphosphonyl-L-leucyl)-4-(2-furyl)]-L-phenylalanine dilithium salt (Compound 1)

a) Preparation of N-[N'-(tert-butoxycarbonyl)-L-leucyl]-[4-(2-furyl)]-L-phenylalanine methyl ester Dicyclohexylcarbodiimide (1.75 g; 8.50 mmoles) was added to a solution of N-(tert-butoxycarbonyl)-L-leucine monohydrate (0.98 g; 3.93 mmoles) and N-hydroxysuccinimide (0.45 g; 3.93 mmoles) in 1,4-dioxane (40 ml).

The reaction mixture was kept under stirring for a hour at room temperature and, subsequently, the formed dicyclohexylurea was filtered off.

(2-furyl)]-L-phenylalanine methyl ester (0.75 g; 3.27 mmoles), prepared according to the synthetic method described by W. C. Shieh in J. Org. Chem, 1992, 57, 379–381, was then added to the obtained solution.

The reaction mixture was kept under stirring for 18 hours and, subsequently, the solvent was evaporated at reduced pressure.

The obtained residue was collected with ethyl ether and the mixture was filtered again.

The solvent was thus evaporated at reduced pressure and the resultant crude was purified by silica gel flash chromatography (petroleum ether:ethyl acetate=75:25; pressure of nitrogen 0.1 atm) furnishing N-[N'-(tert-butoxycarbonyl)-L-leucyl]-[4-(2-furyl)]-L-phenylalanine methyl ester (0.98 g; 30% yield), as a white solid.

$^1$H-NMR (200 MHz, CDCl$_3$): δ (ppm): 0.85–0.93 (2d, 6H); 1.4 (s, 9H); 1.50–1.70 (m, 3H); 3.00–3.20 (m, 2H); 3.70 (m, 3H); 4.00–4.12 (m, 1H); 4.70–4.90 (m, 2H); 6.52 (d, 1H); 6.41–7.41 (m, 3H); 7.1–7.6 (m, 4H).

b) Preparation of N-(L-leucyl)-[4-(2-furyl)]-L-phenylalanine methyl ester hydrochloride Thionyl chloride (0.31 ml; 4.28 mmoles) was added at 0° C. to a solution of N-[N'-(tert-butoxycarbonyl)-L-leucyl]-[4-(2-furyl)]-L-phenylalanine methyl ester (0.98 g; 2.14 mmoles), prepared as described in example 1a, in methanol (20 ml).

The reaction mixture was kept under stirring at room temperature for 24 hours and the solvent was then evaporated at reduced pressure furnishing N-(L-leucyl)-[4-(2-furyl)]-L-phenylalanine methyl ester hydrochloride (0.79 g; 93% yield), used as such in the subsequent reaction.

c) Preparation of N-[N'-(phenoxy)(propyl)phosphoryl-L-leucyl]-[4-(2-furyl)]-L-phenylalanine A solution of phenol (0.28 g; 3.00 mmoles) and triethylamine (0.42 ml; 3.00 mmoles) in methylene chloride (17 ml) was slowly added dropwise to a solution of propylphosphonic dichloride (0.37 ml; 3.00 mmoles) in methylene chloride (4 ml), cooled at 0° C. and under nitrogen.

A mixture of N-(L-leucyl)-[4-(2-furyl)]-L-phenylalanine methyl ester hydrochloride (0.79 g; 2.00 mmoles), prepared as described in example 1b, and triethylamine (0.7 ml; 5.00 mmoles) in methylene chloride (5 ml) was then added dropwise to the reaction mixture, kept under stirring at room temperature for 3 hours and subsequently cooled at 0° C.

The reaction mixture was kept under stirring at room temperature for 3 hours and water was then added.

The phases were separated and the organic phase was dried on sodium sulphate and evaporated at reduced pressure.

The resultant residue was purified by silica gel flash chromatography (eluent petroleum ether:ethylacetate=1:1; pressure of nitrogen 0.1 atm) finishing N-[N'-(phenoxy)(propyl)phosphoryl-L-leucyl]-[4-(2-furyl)]-L-phenylalanine methyl ester (0.4 g; 40% yield), as a white solid.

$^1$H-NMR (200 MHz, CDCl$_3$): δ (ppm): 0.70–1.90 (m, 16H); 2.90–3.20 (m, 2H); 3.35–3.51 (m, 1H); 3.65 (s, 3H); 3.70–3.90 (m, 1H); 4.65–4.80 (m, 1H); 6.70–6.85 (m, 1H); 6.40–7.40 (m, 3H); 7.00–7.60 (m, 9H).

d) Preparation of N-(N'-propylphosphonyl-L-leucyl)-[4(2-furyl)]-L-phenpylalanine dilithium salt A solution of lithium hydroxide monohydrate (90 mg; 2.16 mmoles) in water (2 ml) was added to the solution of N-[N'-(phenoxy)(propyl)phosphoryl-L-leucyl]-[4-(2-furyl)]-L-phenylalanine methyl ester (0.4 g; 0.72 mmoles), prepared as described in example 1c, in tetrahydrofuran (5 ml).

The reaction mixture was kept under stirring at room temperature for a hour.

The mixture was subsequently evaporated at reduced pressure and the obtained residue was collected with ethanol and evaporated again, repeating twice this procedure.

The residue was then collected with ethyl acetate and the mixture was kept under stirring at room temperature for 24 hours.

The mixture was then filtered affording N-(N'-propylphosphonyl-L-leucyl)-[4-(2-furyl)]-L-phenylalanine dilithium salt (0.3 g; 90% yield) as a white solid.

$^1$H-NMR (200 MHz, D$_2$O): δ (ppm): 0.58–0.73 (m, 9H); 0.98–1.46 (m, 7H); 2.71–3.11 (m, 2H); 3.26–3.38 (m, 1H); 4.27–4.33 (m, 1H); 6.39 (dd, 1H); 6.63 (d, 1H); 7.33 (d, 1H); 7.10–7.52 (m, 4H).

EXAMPLE 2

N-(N'-propylphosphonyl-L-valyl)-[4-(2-thiazolyl)]-L-phenylalanine dilithium salt (Compound 2)

By working as described in example 1 through steps a–d, the following compounds were prepared:

a) Preparation of N-[N-'-(tert-butoxycarbonyl)-L-valyl]-[4-(2-thiazolyl)]-L-phenylalanine methyl ester $^1$H-NMR (200 MHz, CDCl$_3$): δ (ppm): 0.80–0.95 (m, 6H, C$\underline{H}_3$—CH—C$\underline{H}_3$); 1.42 [s, 9H, C(CH$_3$)$_3$]; 2.00–2.19 (m, 1H, CH$_3$—C$\underline{H}$—CH$_3$); 3.03–3.22 (m, 2H, C$\underline{H}_2$-phenylene); 3.70 (s, 3H, COOCH$_3$); 3.83–3.93 (m, 1H, NH—C$\underline{H}$—CH); 4.72–5.05 (m, 2H, NHCOO, CHCOO); 6.40 (bd, 1H, N$\underline{H}$—CH—COO); 7.13–7.90 (m, 6H, aryl).

b) Preparation of N-(L-valyl)-[4-(2-thiazolyl)]-L-phenylalanine methyl ester hydrochloride $^1$H-NMR (200 MHz, D$_2$O): δ (ppm): 0.77–0.83 (m, 6H, C$\underline{H}_3$—CH—C$\underline{H}_3$); 1.93–2.10 (m, 1H, CH$_3$—C$\underline{H}$—CH$_3$); 2.96–3.21 (m, 2H, C$\underline{H}_2$-phenylene); 3.55 (s, 3H, COOCH$_3$); 3.62 (d, 1H, C$\underline{H}$-NH$_2$); 4.60–4.70 (m, 1H, CH—COO); 7.25–7.74 (m, 4H, phenylene); 7.64–7.87 (m, 2H, thiazolyl).

c) Preparation of N-[N'-(phenoxy)(propyl)phosphoryl-L-valyl]-[-4-(2-thiazolyl)]-L-phenylalanine methyl ester $^1$H-NMR (200 MHz, CDCl$_3$): δ (ppm): 0.70–1.07 (m, 9H, C$\underline{H}_3$—CH—C$\underline{H}_3$, C$\underline{H}_3$—CH$_2$); 1.50–2.00 (m, 5H, C$\underline{H}_2$—C$\underline{H}_2$—P—NH—CH—C$\underline{H}$); 2.90–3.18 (m, 2H, C$\underline{H}_2$-phenylene); 3.22–3.70 (m, 2H, P—NH—CH); 3.64 (s, 3H, COOCH$_3$); 4.71–4.87 (m, 1H, CH—COO); 6.75–6.86 (m, 1H, NHCO); 7.05–7.89 (m, 11H, aryl).

d) Preparation of N-(N'-propylphosphonyl-L-valyl)-[4-(2-thiazolyl)]-L-phenylalanine dilithium salt $^1$H-NMR (200 MHz, D$_2$O): δ (ppm): 0.40–0.80 (m, 9H, C$\underline{H}_3$—CH—C$\underline{H}_3$, C$\underline{H}_3$—CH$_2$); 1.00–1.70 (m, 5H, C$\underline{H}_2$—C$\underline{H}_2$—P—NH—CH—C$\underline{H}$); 2.75–3.24 (m, 3H, P—NH—C$\underline{H}$, C$\underline{H}_2$-phenylene); 4.25–4.39 (m, 1H, CH—COO); 7.16–7.70 (m, 6H, aryl).

EXAMPLE 3

In vitro Evaluation of the Pharmacologic Activity a) NEP-inhibitory activity

The NEP-inhibitory activity was evaluated in rat kidney cortex membranes prepared according to the procedure described by T. Maeda et al. in Biochim Biophys. Acta 1983, 731(1), 115–120.

By working at 0–4° C. kidneys were removed from male Sprague-Dawley rats weighing approximately 300 g.

Cortex was carefully dissected, finely minced and suspended in a homogenization buffer (10 mM sodium phosphate pH 7.4 containing 1 mM MgCl2, 30 mM NaCl, 0.02% NaN3) 1:15 weight/volume.

The tissue was then homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage.

The membranes were stored in small aliquots at −80° C. until use.

The NEP-inhibitory activity was evaluated according to the method described by C. Llorens et al., in Eur. J. Pharmacol., 69, (1981), 113–116, as reported hereinafter.

Aliquots of the membrane suspension prepared as above described (concentration 5 μg/ml of proteins) were preincubated in the presence of an aminopeptidase inhibitor (Bestatin–1 mM) for 10 minutes at 30° C. [$^3$H][Leu$^5$]-enkephaline (15 nM) and buffer TRIS/HCl pH 7.4 (50 mM) were added in order to obtain a final volume of 100 μl.

Incubation (20 minutes at 30° C.) was stopped by adding HCl 0.1M (100 μl).

The formation of the metabolite [$^3$H]Tyr-Gly-Gly was quantified, after separation of the unreacted substrate by chromatography on polystirene columns (Porapak Q), by measuring the relative radioactivity through liquid scintillation.

The percentage of inhibition of the metabolite formation in the membrane preparations treated with the compounds of formula I and with the comparative compounds with respect to the untreated membrane preparations was expressed as IC$_{50}$ (nM) value.

b) ACE-inhibitory activity

The ACE-inhibitory activity was evaluated according to the method reported in the literature by B. Holmquist et al., in Analytical Biochemistry 95, 540–548 (1979).

50 μM of ACE (250 mU/ml purified by lung rabbit, EC 3.4.15.1 SIGMA) were preincubated with 50 μl of the compounds of formula I or with the comparison compounds in thermostated cuvettes at 37° C.

The reaction was started by adding furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curves, the absorbance at 340 nm was recorded in continuo for 5 minutes.

The inhibition of the enzymatic activity of the compounds of formula I and of the comparison compounds was expressed as IC$_{50}$ (nM) value.

The compounds of formula I were tested as lithium salts.

The IC$_{50}$ (nM) values related to the ACE-inhibitory and NEP-inhibitory activity of the compounds 1 and 2 and of the comparison compounds R-1, Thiorphan and Captopril are reported in the following table 1.

Table 1

NEP-inhibitory and ACE-inhibitory activity, expressed as IC$_{50}$ (nM) value, of the compound 1, of the compound 2, of the compound R-1, of Thiorphan and of Captopri.

| Compound | ACE-inhibitory activity IC$_{50}$ (nM) | NEP-inhibitory activity IC$_{50}$ (nM) |
|---|---|---|
| 1 | 5.7 | 6.0 |
| 2 | 9.4 | 2.7 |
| R-1 | 20.0 | 5.5 |
| Thiorphan | 98.6 | 11.3 |
| Captopril | 2.8 | not active |

The data reported in table 1 show that the compounds of formula I, object of the present invention, are endowed with a significant dual ACE/NEP-inhibitory activity. Said activity resulted to be comparable to that of Captopril, to what it concerns the ACE-inhibitory activity, and to that of Thiorphan, to what it concerns the NEP-inhibitory activity.

Moreover, the dual ACE/NEP-inhibitory activity of the compounds of formula I resulted to be significantly higher than that of the compound R-1.

EXAMPLE 4

Ex vivo Evaluation of the Pharmacologic Activity
a) NEP-inhibitory activity

The ex vivo NEP-inhibitory activity was evaluated according to the method reported in the literature by M. Orlowsky et aL, in Biochemistry 1981, 20, 4942–4950.

The inhibitory activity of the compounds of formula I and of the compound R-1 was evaluated in kidneys of spontaneously hypertensive rats (SHR), 5 minutes after i.v. injection of the tested compounds (21 μmoles/Kg).

After the removal of the kidneys from SHR, the renal tissue was homogenized and incubated for 15 minutes at 37° C. in the presence of Glutaryl-Ala-Ala-Phe-2-naphthyliamide (GAAP), as a substrate, and aminopeptidase M at pH 7.6. The reaction was stopped by adding an aqueous solution at 10% of trichloroacetic acid.

The released 2-naphthylamine was determined by adding fast garnet dye (2 ml). Enzyme reaction rates were determined by measuring the increase in the optical density at 524 nm ($OD_{524}$) with respect to a standard obtained with 2-naphthylamine complexed with fast garnet.

The NEP-inhibitory activity of the compounds of formula I and of the compound R-1 was expressed as percentage of inhibition in SHR kidneys.

b) ACE-inhibitory activity

The ex vivo ACE-inhibitory activity was evaluated by using a radiometric method, as reported in the literature by J. W. Ryan et al. in Biochem J. (1977), 167, 501–504.

The inhibitory activity of the compounds of formula I and of the compound R-1 was evaluated in lungs of spontaneously hypertensive rats (SHR), 5 minutes after i.v. injection of the tested compounds (21 μmoles/Kg).

After the removal of the lungs from SHR, the lung tissue was homogenized and incubated for 2 hours at 37° C. in the presence of [$^3$H]Hyp-Gly-Gly, as a substrate.

The reaction was stopped by adding hydrochloric acid.

The released radio-labelled hyppuric acid was extracted with ethyl acetate and counted by liquid scintillation spectrometry, according to conventional methods. The ACE-inhibitory activity of the compounds of formula I and of the compound R-1 was expressed as percentage of inhibition in SHR lungs.

The percentage of NEP inhibition and of ACE inhibition, evaluated in kidneys and lungs of SHR respectively, of the compound 1 and of the compound R-1 are reported int the following table 2.

Table 2

NEP-inhibitory and ACE-inhibitory activity, expressed as percentage of inhibtion in SHR kidneys and lungs respectively, after i.v. injection (21 μmoles/kg) of the compound 1 and ofthe compound R-1.

| Compound | NEP-inhibitory activity (kidney) % of inhibition | ACE-inhibitory activity (lung) % of inhibition |
|---|---|---|
| 1 | 70 | 88 |
| R-1 | 20 | 25 |

The data reported in table 2 clearly show that the compounds of formula I, object of the present invention, are endowed with a dual ACE/NEP-inhibitory activity significantly higher than that of the compound R-1.

What is claimed is:

1. A compound of formula

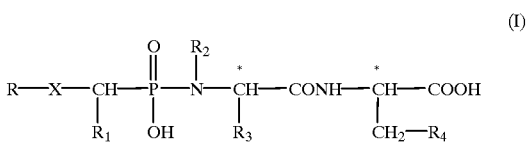

wherein

R is a straight or branched $C_1$–$C_6$ alkyl group optionally substituted with one or more fluorine atoms, an aryl or arylalkyl group with from 1 to 6 carbon atoms in the alkyl moiety wherein the aryl is a phenyl, 1-naphthyl 2-napithyl group or a 5 or 6 membered aromatic heterocycle with 1 or 2 heteroatoms selected among nitrogen, oxygen and sulphur, optionally substituted with one or more substituents, the same or different, selected among halogen atoms, hydroxy groups, alkyl alkoxy, alkylthio, alkylsuphonyl or alkoxycarbonyl groups with from 1 to 3 carbon atoms in the alkyl moiety, carboxy groups, aminocarbonyl groups, acylamino groups, aminosulphonyl groups, mono- or di-alkylaminocarbonyl groups with from 1 to 3 carbon atoms in the alkyl moiety;

$R_1$ and $R_2$, the same or different, represent a hydrogen atom or a straight or branched $C_1$–$C_4$ alkyl group;

$R_3$ is a straight or branched $C_1$–$C_6$ alkyl group or an arylalkyl group with from 1 to 6 carbon atoms in the alkyl moiety wherein the aryl is a phenyl, 1-naphthyl, 2-naphthyl group or a 5 or 6 membered aromatic heterocycle with one or two heteroatoms selected among nitrogen, oxygen and sulphur, optionally substituted as indicated for R;

$R_4$ is a 5 or 6 membered aromatic heterocyclic group with one or two heteroatoms selected among nitrogen, oxygen and sulphur, substituted with a 5 or 6 membered aromatic heterocyclic group with one or two heteroatoms selected among nitrogen, oxygen and sulphur or with a phenyl group, or it is a phenyl group substituted with a 5 or 6 membered aromatic heterocyclic group with one or two heteroatoms selected among nitrogen, oxygen and sulphur, wherein the phenyl and the heterocyclic groups are optionally substituted with one or more substituents, the same or different, selected among halogen atoms, alkyl, alkoxy, alkylthio or alkoxycarbonyl groups with from 1 to 3 carbon atoms in the alkyl moiety;

X is a single bond or an —O—CONH— or —CONH— group;

the carbon atoms marked with an asterisk are asymmetric carbon atoms;

and pharmaceutically acceptable salts thereof;

provided that $R_4$ is not an imidazolyl or indolyl group.

2. A compound according to claim 1 wherein $R_4$ represents a phenyl group substituted in position 4 with a heterocyclic group.

3. A compound according to claim 2 wherein $R_1$ and $R_2$ represent a hydrogen atom and $R_3$ represents a straight or branched $C_1$–$C_4$ alkyl group.

4. A compound according to claim 1 in the form of a salt with an alkali metal selected among sodium, lithium and potassium.

5. A process for preparing a compound as recited in claim 1 comprising
(a) reacting a phosphorylated derivative of formula II

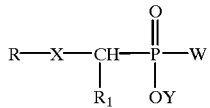

(II)

wherein R, $R_1$ and X have the meanings reported in claim 1, W represents a halogen atom and Y represents a protective group selected among a $C_1$–$C_4$ alkyl, a phenyl or a phenylalkyl with from 1 to 4 carbon atoms in the alkyl moiety;
with a dipeptide of formula III

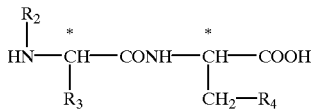

(III)

wherein $R_2$, $R_3$, $R_4$ have the meanings reported in claim 1, and wherein the carboxyl group is protected; for a time and under conditions effective for the amino group of formula III to displace the halogen atom of formula II;

(b) removing the protective groups;

(c) isolating the compound of formula I.

6. A compound of formula I according to claim 1 selected between N-(N'-propylphosphonyl-L-leucyl-[4-(2-furyl)]-L-phenylalanine and N-(N'-propylphophonyl-L-valyl)-[4-(2-thiazolyl)]-L-phenylalanine.

7. A composition comprising a compound according to claim 1 in combination with a pharmaceutically acceptable carrier.

8. A method of inhibiting ACE (angiotensin converting enzyme) and NEP (neutral endopeptidase) comprising administering a compound according to claim 1 to a patient in need thereof for a time and under conditions effective to inhibit ACE and NEP.

* * * * *